US00PP22498P2

(12) United States Plant Patent
Kordes

(10) Patent No.: US PP22,498 P2
(45) Date of Patent: Feb. 21, 2012

(54) SHRUB ROSE PLANT NAMED 'KORKUPMUL'

(50) Latin Name: *Rosa hybrida*
Varietal Denomination: KORkupmul

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/925,236

(22) Filed: Oct. 14, 2010

(51) Int. Cl.
*A01H 5/00* (2006.01)

(52) U.S. Cl. ..... Plt./104

(58) Field of Classification Search ..... Plt./104
See application file for complete search history.

*Primary Examiner* — Kent L Bell

(57) ABSTRACT

A new and distinct variety of rose with long lasting, novel yellow flowers, and attractive foliage with good disease resistance. It exhibits upright to bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORkupmul'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 1998. The crossing was between an unnamed seedling and another unnamed seedling.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORkupmul'.

SUMMARY OF THE INVENTION

The new rose plant may be distinguished from its seed parent, an unnamed seedling, by the following combination of characteristics:

1. The open flower diameter of 'KORkupmul' is 90 mm. The open flower size diameter of the unnamed seedling is 110 mm.
2. 'KORkupmul' has, on average, 80-90 petals per flower. The unnamed seedling has, on average, 45 petals per flower.

The new rose plant may be distinguished from its pollen parent, an unnamed seedling, by the following combination of characteristics:

1. The common color of 'KORkupmul' is yellow. The common color of the unnamed seedling is pink.
2. 'KORkupmul' exhibits bushy, erect growth. The unnamed seedling exhibits arching growth.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORgohowa' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORkupmul' was selected in May, 1999 from the seedling beds to be asexually propagated for further evaluation. The first asexual propagation of 'KORkupmul' was done by budding to seedling understocks in July, 1999 at the inventor's nursery in Offenseth-Sparrieshoop, Germany.

This initial and other subsequent propagations conducted in controlled environments demonstrate that 'KORkupmul' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, flowers, leaves, and stems of 'KORkupmul'.

DETAILED BOTANICAL DESCRIPTION

The following is a description of 'KORkupmul', as observed growing in October, 2010 in a nursery in Jackson County, Oreg. on plants of 5 years of age. Color references are made using The Royal Horticultural Society (London, England) Colour Chart, 2001 except where common terms of color are used.

For a comparison, several physical characteristics of the rose variety 'KORquelda', a rose variety from the same inventor described and illustrated in U.S. Plant Pat. No. 17,048 and issued on Aug. 22, 2006 are compared to 'KORkupmul' in Chart 1.

CHART 1

| Characteristic | 'KORkupmul' | 'KORquelda' |
|---|---|---|
| Petal count | 80-90 | 40 |
| Plant height | 130 cm | 100 cm |
| Disease resistance | High | Moderate |

Parents:

*Seed parent.*—An unnamed seedling.

*Pollen parent.*—An unnamed seedling.

Classification:

*Botanical classification.*—*Rosa hybrida*, 'KORkupmul'.

*Commercial classification.*—Shrub rose.

FLOWER AND FLOWER BUD

Blooming habit: Recurrent.

Flower bud:

*Size.*—Upon opening, 30 mm in length from base of receptacle to end of bud and 20 mm diameter at its widest point.

*Bud form.*—Short. Broad based.

*Bud color.*—As sepals first unfold, bud color is Yellow Group 1B. When ¼ open, the upper surface of petals is Yellow Group 1D, and the lower surface is Yellow Group 1C.

*Sepals.*—Size: Average 25-30 mm long×12 mm wide. Shape: Sepals generally acuminate. Sepal apex is generally cirrose. Weak foliaceous appendages on three of the five sepals. Base is flat at union with receptacle. Quantity: Five. Margins: With fine hairs and stipitate glands. Surface texture: Inner side: Covered in fine hairs. Outer surface: Smooth. Stipitate glands are present. Color: Upper surface Green Group 138B with intonations of Gray-Red Group 182B. Lower surface Yellow-Green Group 144A.

Receptacle:

*Surface.*—Smooth.

*Color.*—Yellow-Green Group 144A.

*Shape.*—Funnel.

*Size.*—10 mm (h)×12 mm (w).

Peduncle:

*Surface.*—Smooth.

*Length.*—45 mm average length.

*Diameter.*—4 mm average diameter.

*Color.*—Yellow-Green Group 144A.

*Strength.*—Moderate.

*Borne.*—Multiple flower buds per stem, generally 3 to 6.

Flower bloom:

*Fragrance.*—Moderate.

*Duration.*—On the plant 11 days. Long lasting. As a cut flower, 5 to 7 days. Senesced petals drop away cleanly.

*Size.*—Medium flowered garden rose. When open, the average flower diameter is 90 mm and the average flower height is 45 mm.

*Form.*—Shape of flower when viewed from the side: Upon opening, upper part: Convex. Upon opening, lower part: Flat. Open flower, upper part: Flattened convex. Open flower, lower part: Flat.

Color:

*Upon opening, petals.*—Outermost petals: Outer Side: Yellow Group 10D. Inner Side: Yellow Group 11D. Innermost petals: Outer Side: Yellow Group 12A. Inner Side: Yellow Group 12B.

*Upon opening, basal petal spots.*—Basal petal spot, outermost petals: Outer Side: Yellow Group 13A. Inner Side: Yellow-Orange Group 14A. Basal petal spot, innermost petals: Outer Side: Yellow Group 13B. Inner Side: Yellow-Orange Group 14B.

*After opening, petals.*—Outermost petals: Outer Side: Yellow Group 8D. Inner Side: Yellow Group 10D. Innermost petals: Outer Side: Yellow Group 1C. Inner Side: Yellow Group 2C.

*After opening, basal petal spots.*—Basal petal spot, outermost petals: Outer Side: Yellow Group 2B. Inner Side: Yellow Group 8A. Basal petal spot, innermost petals: Outer Side: Yellow Group 13B. Inner Side: Yellow Group 13C. Variegations: None.

General Tonality: On open flower Yellow Group 4A. No change in the general tonality at the end of the 8th day. Afterwards, general tonality is Yellow Group 4D.

Petals:

*Petal count.*—Approximately 80-90 petals under normal conditions.

*Petal reflex.*—Petals reflex slightly.

*Petal edge.*—Entire.

*Petal shape.*—Round. Apex shape is round. Shape of base is rounded.

*Petal size.*—40 mm long; 35 mm wide.

*Thickness.*—Average.

*Petal arrangement.*—Generally in a regular pattern with overlapping edges.

Petaloids: Present.

*Petaloid count.*—Average of 8-12 per flower.

*Petaloid edge.*—Entire.

*Petaloid texture.*—Smooth.

*Petaloid shape.*—Deltoid.

*Petaloid size.*—Petaloids are 12 mm long and 8 mm wide.

*Petaloid color.*—Color of inner side is Yellow Group 1D. Color of outer side is Yellow Group 1C.

Reproductive organs:

*Pistils.*—Approximately 40-50 present. Stigmas: Location: Slightly inferior in position to anthers. Color: Yellow-Orange Group 20B. Styles: Length: 3 mm long. Color: Yellow-Orange Group 20A. Intonations of Red Group 40B.

*Stamens.*—Approximately 65-75 on average and regularly arranged. Anthers: Size: 1 mm long. Color: Yellow-Orange Group 21B. Pollen: Generally present. Color: Yellow-Orange Group 21B. Filaments: Color: Yellow Group 8C. Length: 8 mm.

THE PLANT

*Plant growth.*—Moderate vigor. Upright to bushy habit. When grown as a budded nursery plant the average plant height is 130 cm and the average plant width is 70 cm.

*Stems.*—Stem color: Young wood: Yellow-Green Group 144A with intonations of Gray-Red Group 182A. Older wood: Yellow Group 144A. Stem surface: Young wood: Smooth. Older wood: Smooth.

*Prickles.*—Present. Incidence: 8-12 per 10 cm of juvenile stem. 5-7 per 10 cm of mature stem. Size: Average length: 12 mm. Color: Immature prickles: Red Group 182A. Mature prickles: Gray-Brown Group 199D. Senescing to Gray-Brown Group 199B. Shape: Concave. Anthocyanin: Color Gray-Red Group 182A.

*Leaves and leaflets.*—Normally 5 leaflets on normal leaves in middle of the stem. Venation pattern: Pyramidal net pattern. Leaf size: 170 mm (1)×140 mm (w). Quantity: Abundant. Texture: Upper side of leaflet: Glossy. Smooth. Leathery. Under side of leaflet: Semi glossy. Smooth. Leathery. Color, mature foliage: Upper Leaf Surface: Green Group 137A. Lower Leaf Surface: Green Group 138B. Color, juvenile foliage: Upper Leaf Surface: Green Group 137A. Lower Leaf Surface: Green Group 138B. Anthocyanin intonation: Present. Location: Intonations present on juvenile leaf margins. Color: Gray-Purple Group 187B.

*Stipules.*—Size: 18 mm long. 8 mm between the tips of the stipule. Main body of stipule 2-3 mm in width. Shape: Longitudinally flanged. Stipule color: Yellow-Green Group N144A. Anthocyanin: Gray-Red Group 182A. Presence of stipitate glands: Present on margins. Margins: Ciliated with stipitate glands.

*Petiole.*—Length: 25 mm. Diameter: 2-3 mm. Petiole color: Upper side: Yellow-Green Group 144C. Lower side: Yellow-Green Group 144B. Underneath: A few small prickles underneath. Stipitate glands: Limited numbers of stipitate glands on margins.

*Petiole rachis.*—Length: 45 mm. Diameter: 2 mm. Color: Yellow-Green Group 144B. Anthocyanin present on juvenile tissue. Color: Gray-Red Group 182B. Margins: Entire. Prickles: A few small prickles underneath. Stipitate glands: Limited numbers of stipitate glands on margins.

*Leaflets.*—Size: Average size of the terminal leaflet is 70 mm (1)×45 mm (w). Shape: Ovate. Base: Ovate. Apex: Acute. Margins: Serrated. Texture: Leathery.

Hips/seed formation: Observed. Size: 20 mm (1)×20 mm (w). Color: Yellow-Green Group 144B.

Winter hardiness: To date, the variety has been grown successfully in Zone 5.

Disease resistance: Excellent resistance to Powdery mildew (*Sphaerotheca pannosa*) and blackspot (*Diplocarpon rosae*) diseases under normal growing conditions.

I claim:

1. A new and distinct variety of rose plant, as described and illustrated herein.

* * * * *

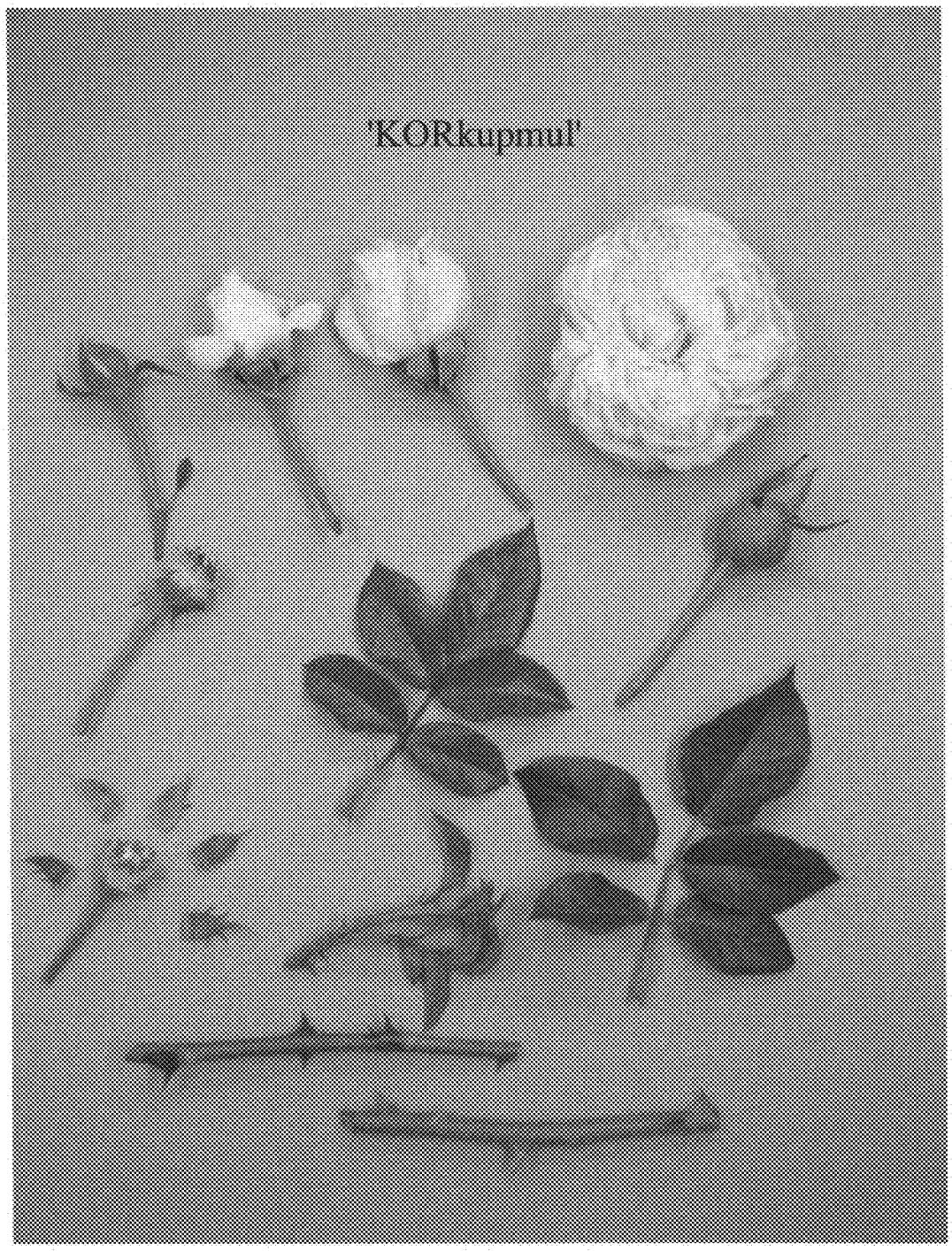
'KORkupmul'